(12) United States Patent
Franck

(10) Patent No.: US 12,201,472 B2
(45) Date of Patent: Jan. 21, 2025

(54) FETAL ULTRASOUND PROCESSING UNIT

(71) Applicant: KONINKLIJKE PHILIPS N.V., Eindhoven (NL)

(72) Inventor: Christoph Florian Franck, Magstadt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 430 days.

(21) Appl. No.: 17/606,130

(22) PCT Filed: Apr. 22, 2020

(86) PCT No.: PCT/EP2020/061112
§ 371 (c)(1),
(2) Date: Oct. 25, 2021

(87) PCT Pub. No.: WO2020/216753
PCT Pub. Date: Oct. 29, 2020

(65) Prior Publication Data
US 2022/0296209 A1    Sep. 22, 2022

(30) Foreign Application Priority Data
Apr. 24, 2019 (EP) ..................................... 19170870

(51) Int. Cl.
*A61B 8/08*    (2006.01)
*A61B 8/00*    (2006.01)

(52) U.S. Cl.
CPC ............ *A61B 8/0866* (2013.01); *A61B 8/488* (2013.01); *A61B 8/5223* (2013.01); *A61B 8/58* (2013.01)

(58) Field of Classification Search
CPC ... A61B 8/488; A61B 8/0866; A61B 5/02411; A61B 2090/378; A61B 2090/364; A61B 8/58; A61B 8/52; A61B 8/5223
See application file for complete search history.

(56) References Cited

U.S. PATENT DOCUMENTS

| 4,984,576 A | 1/1991 | Schulenberg |
| 2013/0158407 A1 | 6/2013 | Kabakov |
| 2014/0276070 A1 | 9/2014 | Kabakov |

FOREIGN PATENT DOCUMENTS

| WO | 9000368 A1 | 1/1990 | |
| WO | 2010143113 A1 | 12/2010 | |
| WO | WO-2017045915 A1 * | 3/2017 | ............... A61B 8/02 |

OTHER PUBLICATIONS

Karimi Rahmati A., A PCA/ICA based Fetal ECG Extraction from Mother Abdominal Recordings by Means of a Novel Data-driven Approach to Fetal ECG Quality Assessment, Mar. 1, 2017 (Year: 2017).*

(Continued)

*Primary Examiner* — Gerald Johnson

(57) ABSTRACT

An ultrasound processing unit and method for use in ultrasound fetal monitoring are provided. The processing unit is configured to receive Doppler ultrasound data corresponding to one or more initial trial depth windows within the fetal region. From these, an ultrasound signal for each trial depth window is extracted. Unlike approaches of the state of the art that seek the optimum depth range based on signal strength, in the present disclosure a defined measure of statistical structure of the signal is computed for each depth signal, wherein the measure of statistical structure corresponds to an intrinsic statistical property or characteristic of the signal. A new recording window is then selected for acquiring a fetal heart rate signal, based on selecting a window which is estimated to maximize the measure of statistical structure of ultrasound signals derived from the new window.

15 Claims, 1 Drawing Sheet

(56) References Cited

OTHER PUBLICATIONS

International Search Report and Written Opinion, International Application No. PCT/EP2020/061112, Mailed on Jun. 2, 2020.
Hyvarinen, A. et al., "Independent component analysis: algorithms and applications", Neural Networks, Elsevier Science Publishers, vol. 13, No. 4-5, Jun. 2000.
Hamelmann, P. et al., "Improved ultrasound transducer positioning by fetal heart location estimation during Doppler based heart rate measurements", Physiological Measurement, vol. 38, No. 10, Sep. 2017.

* cited by examiner (a) (b)

FETAL ULTRASOUND PROCESSING UNIT

CROSS-REFERENCE TO PRIOR APPLICATIONS

This application is the U.S. National Phase application under 35 U.S.C. § 371 of International Application No. PCT/EP2020/061112, filed on 22 Apr. 2020, which claims the benefit of European Patent Application No. 19170870.0, filed on 24 Apr. 2019. These applications are hereby incorporated by reference herein.

FIELD OF THE INVENTION

The invention provides an ultrasound processing unit, in particular for identifying individual heart rate signals within Doppler ultrasound data.

BACKGROUND OF THE INVENTION

Electronic fetal monitoring (EFM) comprises different methods of recording vital signs, such as pulse rate, of a fetus during pregnancy and labor. A common method used by EFM systems is the detection of the fetal heart rate (FHR) by Doppler ultrasound.

This is usually performed by placing a Doppler ultrasound transducer on the maternal abdomen and adjusting the position of the transducer so that fetal pulse rate sources (such as the fetal heart or large fetal arteries) are inside the volume covered by the ultrasound pulses emitted by the transducer. Transmitted ultrasound pulses are reflected from moving internal structures. By detecting frequency shifts (Doppler shifts) in the reflected signals, a fetal pulse signal is generated. This may then be analyzed by the EFM system and the detected fetal pulse rate may be displayed and/or recorded.

The Ultrasound (US) Doppler transducer used for this purpose typically utilizes an unfocused, approximately cylindrical ultrasound beam field. An extent of the beam volume is defined by a characteristic reception time window. During this window the US transducer is set to acquire reflected signals from any moving anatomical structures.

In particular, usually the ultrasound transducer alternates between two modes in quick succession: transmission mode, comprising generating an ultrasound pulse, and receive mode comprising receiving the reflections of the previously emitted ultrasound pulse. A latency or pause period may be present in between.

By modifying the delay between the end of the transmit phase and the start of the reception phase, and by modifying the duration of the transmit phase or the reception phase, it is possible to limit the reception of reflected ultrasound to a certain depth range. This can be used for example to limit the reception to a depth that contains one or more pulse signal sources, and exclude depth ranges that do not contain any pulse signal sources, but contribute to the noise level of the recorded signal.

The depth range from which signals are recorded is also called a 'window'. Windows are usually subsets of the total depth range ('total ultrasound field-of-view') from which a transducer is able to receive signals.

A process of adjustment of the depth window is illustrated in FIG. 1 which schematically depicts US observation of the fetal area at different depths. FIG. 1(a) schematically depicts a deep observation area, and FIG. 1(b) depicts a shallower observation area. For FIG. 1(a), the timing and duration of the receive window of the ultrasound transducer 12 is adjusted, relative to the timing and duration of the US transmission, so that US reflections are detected from a greater depth. As a result a deeper observation volume 14 is obtained. Conversely, in FIG. 1(b), the receive window is adjusted so that US reflections from a shallower depth are detected, resulting in a shallower depth volume 14.

Generally, algorithms for adjusting ultrasound window size and depth will seek to minimize the size of the window as much as possible, as smaller reception windows lead to less noise in the recorded signal. U.S. Pat. No. 4,984,576 describes one such example depth selection algorithm for instance.

State of the art EFM units such as this may use an iterative approach to determine an optimum depth range to use. In particular, the iterative approach may seek the depth range that contains the largest amount of signal strength, while excluding areas that contribute noise or weaker signal components. In FIG. 1 for example, the shallower depth range of FIG. 1(b) provides the stronger signal since it encompasses the fetal heart, but excludes any noise which might be present at depths below the fetal heart.

The iterative approach may typically use two separate receive windows with independently adjustable start and stop depths. One window is used for the actual signal acquisition. The other window is used to probe whether signal intensity may be increased by including a larger depth range, and/or, whether reducing the depth range will significantly reduce signal intensity. Often, a receive window range that is as small as possible is preferred, as smaller windows typically result in reduced noise.

State of the art depth selection algorithms such as these work optimally when there is only a single pulse rate source within the total ultrasound field-of-view. However, depending on the orientation and the size of the beam field, it is possible that more than one pulse signal source may be present in the field of view: one corresponding to the maternal pulse rate, and one (or more, in the case of multiple pregnancies) fetal pulse rate sources.

The iterative approach described above is not able to discriminate between different pulse signal sources captured in the field-of-view of the transducer unit, e.g. two fetal hearts; or maternal and fetal heart. Rather, it will typically include all detectable pulse rate sources within its calculation, and attempt to incorporate all of these within the selected depth window. As a consequence, the adjustment procedure may result in acquisition of a Doppler ultrasound signal which is a mixture of two or more pulse rate sources. This mixture is difficult to analyze, especially if the two pulse rate source have similar amplitude or power. This can lead to dropouts in the fetal heart rate recording or erroneous heart rates being recorded.

Reduced availability of fetal heart rate (FHR) values or erroneous FHR values can lead to a delay in diagnosis of compromised fetal health or incorrect diagnosis of such a condition.

There would be advantage therefore in providing an improved Doppler ultrasound processing approach, capable of distinguishing different heart rate sources within the input data.

SUMMARY OF THE INVENTION

The invention is defined by the claims.

According to examples in accordance with an aspect of the invention, there is provided an ultrasound processing unit, for use in fetal monitoring for isolating individual heart rate sources within received Doppler ultrasound data, the unit configured to:

receive input Doppler ultrasound data, corresponding to at least one trial depth region within a uterus region of a subject, having a defined height and depth;

extract an ultrasound signal from the ultrasound data corresponding to the at least one trial depth region, and determine a particular measure of statistical structure of the signal;

apply a selection algorithm for determining a depth and height of a new recording region within the subject from which to collect ultrasound signals for measuring a fetal heart rate, the selection algorithm configured to select the window based on the determined measure of statistical structure for the trial region, and based on maximizing the measure of statistical structure of signals acquired from the new recording region. The algorithm thereby seeks to select a new recording depth region which contains only a single (fetal) heart rate source.

Embodiments of the invention are based on use of techniques within statistical signal processing. Embodiments are based on adjusting the recording depth window from which ultrasound (US) signals are acquired based on analysis of one or more statistical properties of the signals.

The measure of statistical structure preferably corresponds to an intrinsic statistical property or characteristics of the ultrasound signal.

Statistical signal processing is an approach which treats signals as stochastic processes, utilizing their statistical properties to perform signal processing tasks or derive information. Statistical techniques are widely used in signal processing applications. For example, in the different field of image processing, the probability distribution of noise incurred when photographing an image may be modeled, and techniques constructed based on this model to reduce the noise in the resulting image. See for example: Scharf, Louis L. (1991). Statistical signal processing: detection, estimation, and time series analysis. Boston: Addison-Wesley.

Embodiments of the invention comprise determining a measure of statistical structure. The measure of statistical structure is preferably an intrinsic property of the ultrasound signal. It is therefore preferably determined based on reference to (e.g. based on processing of) the ultrasound signal alone, without reference to any external entity (e.g. any external signal or information or reference).

Different options exist for the particular measure which is employed, as will be explained further below. In general, the measure of statistical structure refers to a statistical property or characteristic of the signal. It refers to a statistical structuredness of the signal (a degree of statistical structure). The measure of statistical structure essentially refers to a measure of non-randomness or a degree of statistical patterning of the signal. The terms 'measure of statistical structure' and 'measure of non-randomness' of the signal may be used interchangeably for example.

By way of further explanation, the book "Independent component analysis" by A. Hyvärinen, J. Karhunen and E. Oj a discusses for instance three related, but not identical, concepts pertaining to statistical "structure" of a signal.

A first concept of structure relates to a degree of disparity of the probability distribution function of a signal from an equivalent normal distribution (or "Gaussian distribution") having the same mean and variance. This type of statistical structure may be referred to as "non-Gaussianity".

A second measure of statistical structure applies to signals that are time series, i.e. samples that are taken at known points in time and which hence are ordered. In this case, the statistical structure (or non-randomness) corresponds to a degree to which a value at a certain point is at least partially predictable from known earlier values. This measure of structure may be referred to as structure "given by linear autocovariances". This measure of statistical structure is also captured for instance by power spectral density.

A third measure of statistical structure also applies to signals which correspond to time series, but in particular those that exhibit nonstationary of variance, i.e. their variance changes slowly over time. Here the measure of statistical structure corresponds to a degree to which changes in variance can be predicted based on previous groups of samples. Here, while predicting the value of one single sample from previous values may not be possible, changes in variance can be tracked by considering larger contiguous groups of samples.

These measures of statistical structure hence each relate to a degree of statistical patterning or non-randomness of a signal. However, each is effectively independent of the others. Each measure of statistical structure neither implies nor presupposes presence of the others. A signal may in general exhibit one, two or all three types of statistical structure.

The derived measure of signal structure may in certain examples relate to or correspond to one predominant type of statistical structure, or may for instance relate to, or represent, all types of structure that are present in the signal.

The invention is based on the insight that measures of statistical structure of a signal provide a better way to determine the parameters of the ultrasound receive window (the depth region) than signal amplitude/strength/power and allow the electronic fetal monitoring (EFM) system to adjust the depth window height and depth parameters so that only one pulse signal source is included in the ultrasound receive window, even in situations where multiple independent pulse rate sources are present in the possible ultrasound field-of-view.

The statistical structure of a signal can be expressed in different particular properties or characteristics, or in characteristics of different representations of the signal. It can be expressed for instance in the probability density function, linear autocovariances, the power spectral density function or the nonstationarity of the signal's variance. These are examples only, and further examples will be outlined below.

Using a criterion to analyze a trial ultrasound receive window signal which is based, not on signal strength, but on statistical measures of signal structure, solves the above described problem in the state of the art selection algorithms, wherein the algorithm tends to select depth windows containing multiple independent pulse rate sources. As discussed above, this problem occurs because known algorithms use signal strength as a key parameter, which leads to windows with high signal strength, but wherein this is possibly due to multiple pulse sources being present.

Use instead of (preferably intrinsic) statistical characteristics (in particular a degree of statistical structure or non-randomness of acquired signals) avoids this problem. It allows the electronic fetal monitoring system to set the ultrasound receive window parameters so that only one pulse signal source is included in the window even if several sources are present in the total field-of-view, and record a Doppler ultrasound signal from which a pulse rate can be derived without ambiguity.

Different options are possible for the procedure performed by the selection algorithm.

In one set of embodiments, the processing unit may be configured to collect ultrasound signals from a plurality of trial depth regions and wherein the selection algorithm determines the measure of statistical structure for each.

The processing unit may be configured to perform a comparison process to arrive at the new recording window height and depth. The same measure of statistical structure is calculated for each signal, such that the measures may be directly compared.

The comparison process may comprise comparing the measures of statistical structure for the different ultrasound signals with each other. The depth region whose signal has the maximum value for the measure may then be selected as the new recording region or window.

Alternatively, the comparison process may comprise comparing each of the measures with a measure derived for a reference window signal. Again, based on this comparison, a window whose signal achieves the maximum value for the measure of statistical structure in comparison with the reference may be selected as the new recording region or window.

Additionally or alternatively, the selection algorithm may be configured to perform an iterative process, comprising iteratively collecting signals from successive trial depth regions, deriving a measure of statistical structure for each, and comparing the derived measure with that derived for one or more previously trialed windows. This differs from the above described approach, in that signals are collected from different depth regions one at a time and analysis performed after collection of each. In the above described approach, multiple signals are collected from different depth regions and then a comparison process performed using the whole group for instance.

The selection algorithm may comprise selecting the new recording region from among the one or more trial depth regions for which ultrasound data is collected.

Although examples above mention collecting ultrasound signals from a plurality of trial depth regions, selection of the new depth region can be based on data from only one trial depth region in some cases.

For example, a pre-defined threshold for the measure of statistical structure may be pre-stored. The measure of statistical structure derived for the ultrasound signal extracted for the at least one trial depth region may be compared with the predefined threshold. The selection algorithm may be configured to select a trial depth region dependent upon whether the measure of statistical structure for the trial depth region meets, exceeds, or falls within some defined proximity of the predefined threshold.

The predefined threshold may be calculated in advance as a threshold estimated to maximize the measure of statistical structure of the ultrasound signals. In other words, if the measure of statistical structure for a trial depth region meets or falls within a defined proximity of the threshold, there is a high likelihood that it is or is close to a maximum measure of statistical structure. This may be based on empirical testing for example.

The predefined threshold may be based on the measure statistical structure acquired in advance for a reference depth region. For example, the reference depth region referred to above may be one for which a measure of statistical structure has been determined in advance, and wherein the measure of statistical structure derived for the at least one trial depth region is compared with this pre-stored measure for selecting the depth and height of the new recording region.

The above represent only a non-limiting selection of possible examples.

Different options are possible for the measure of statistical structure that is computed for each signal.

The measure of statistical structure of a given signal may include: one or more characteristics of a probability density function for the signal; one or more characteristics of the linear autocovariances of the signal; one or more characteristics of a power spectral density function for the signal, and/or a measure of non-stationarity of the variance of the signal.

Each of the above options will be described in greater detail in the next section.

The measure of statistical structure may include an approximation of one or more of: kurtosis or a derivative thereof, negentropy, autocovariance, autocokurtosis. These options will be described in greater detail in the next section.

The ultrasound processing unit may be operatively coupleable in use with an ultrasound transducer unit, for acquiring the Doppler ultrasound data, and for adjusting acquisition settings of the transducer unit for thereby adjusting a depth region from which ultrasound signals are acquired.

The acquisition settings may include start and stop timings, and durations, of transmit pulses and receive windows of the ultrasound transducers comprised by the ultrasound transducer unit.

Examples in accordance with a further aspect of the invention provide an ultrasound apparatus comprising: an ultrasound processing unit in accordance with any example or embodiment outlined above or described below, or in accordance with any claim of this application; and one or more ultrasound transducers, operatively coupled to the ultrasound processing unit, for providing the Doppler ultrasound data to the ultrasound processing unit, and optionally having adjustable acquisition settings for fixing a depth window of the acquired ultrasound data.

Alternatively, the gating of the data to select a particular depth window may be performed by the processing unit, rather than locally at the ultrasound transducer unit.

The apparatus may comprise an ultrasound probe unit, the probe unit incorporating the ultrasound processing unit and the one or more ultrasound transducers. The probe unit may be a handheld ultrasound probe. The processing unit is integrated in the probe, and the signal processing is performed therefore locally to the probe.

The probe unit may for example have a housing, the ultrasound processing unit and the one or more ultrasound transducers being included within the housing.

Examples in accordance with a further aspect of the invention provide a patient monitoring system comprising: an ultrasound processing unit in accordance with any example or embodiment outlined above or described below, or in accordance with any claim of this application; and a connection interface for connecting in use to an ultrasound transducer unit.

The connection interface may be a wired connector, or may be a wireless connection interface for connecting to a wireless ultrasound probe.

The patient monitoring system may further comprise an ultrasound transducer unit coupled to said connection interface.

The transducer unit may be an ultrasound probe for example.

The ultrasound transducer unit may be only a transmit/receive unit, i.e. comprising one or more ultrasound transducers for transmitting and sensing ultrasound signals. Here, the ultrasound processing unit comprises all signal processing components, including components for digitization and demodulation of the analogue signals output by the transducer unit, to separate signals for one or more different depth regions. In this case, analogue signals are communicated from the transducer unit to the ultrasound processing unit via the communication interface.

In other examples, the ultrasound transducer unit may additionally comprise local, or on-site, signal processing components for performing digitization and demodulation of the signals and to achieve separation of the depth channels. In this case, the resulting digital data representative of the separated signal channels is communicated from the ultrasound transducer unit to the ultrasound processing unit.

The patient monitoring system may include a base station or base unit, to which at least an ultrasound transducer unit, e.g. an ultrasound probe, can be connected. The base station may include a display for displaying results of the processing performed by the ultrasound processing unit.

The patient monitoring system may further include a controller adapted to control acquisition of ultrasound data by a connected transducer unit in use.

The controller may control transmit and receive circuits of the ultrasound transducer unit to acquire the ultrasound signals representative of different depths. The controller may control durations of, and timings between, transmit pulses and receive windows. The controller may control gating of the input Doppler signal data over defined time windows to thereby separate signals corresponding to one or more different depth regions within the subject's tissue.

Examples in accordance with a further aspect of the invention provide an ultrasound processing method for use in fetal monitoring for isolating an individual heart rate source within received Doppler ultrasound data, the method comprising:
  receiving input Doppler ultrasound data, corresponding to at least one trial depth region within a uterus region of a subject, having a defined height and depth;
  extracting an ultrasound signal from the ultrasound data corresponding to the at least one trial depth region, and determining a measure of statistical structure of the signal;
  applying a selection algorithm for determining a depth and height of a new recording region within the subject from which to collect ultrasound signals for measuring a fetal heart rate, the selection algorithm configured to select the window based on the determined measure of statistical structure for the trial region, and based on maximizing the measure of statistical structure of signals acquired from the new recording region.

The method may be a computer implemented method, for example for implementation by a suitable processor, controller or computer.

The measure of statistical structure preferably corresponds to an intrinsic statistical property or characteristic of the signal.

Implementation options and details for each of the above steps may be understood and interpreted in accordance with the explanations and descriptions provided above for the steps performed by the apparatus aspect of the present invention (i.e. the ultrasound processing unit aspect).

Any of the examples, options or embodiment features or details described above in respect of the apparatus aspect of this invention (in respect of the ultrasound processing unit) may be applied or combined or incorporated into the present method aspect of the invention.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
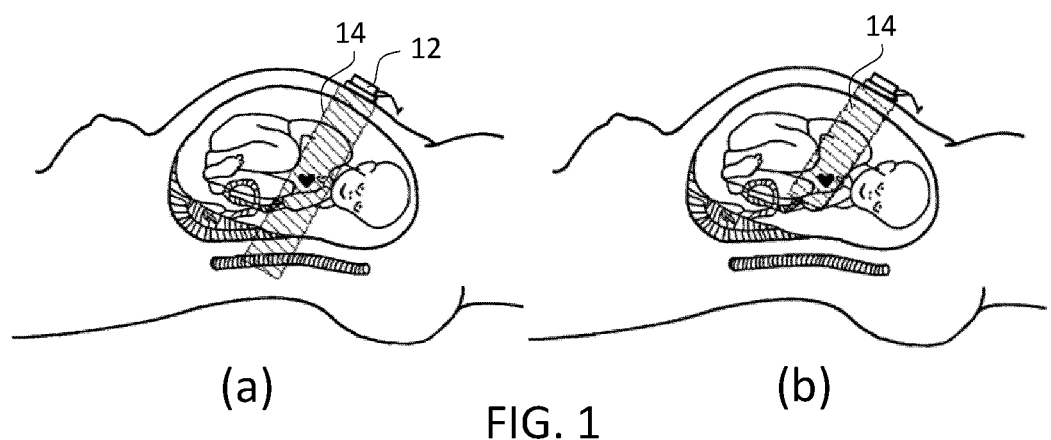
FIG. 1 illustrates a known approach for acquiring fetal heart rate data based on iteratively adjusting a depth of acquired signals.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an ultrasound processing unit and method for use in ultrasound fetal monitoring. The processing unit is configured to receive Doppler ultrasound data corresponding to one or more initial trial depth region (depth windows) within the fetal region. From these, an ultrasound signal for each trial depth region is extracted. For each depth signal, at least one particular measure of statistical structure of the signal is computed. A new recording window is then selected for acquiring a fetal heart rate signal, based on selecting a window which is estimated to maximize the measure of statistical structure of ultrasound signals derived from the new window.

The aim of the invention is identify a depth window for recording ultrasound signals which contains only a single fetal heart rate source. This avoids capturing mixed signals of multiple heart rate sources, which causes inaccuracy.

Prior approaches known in the art select depth windows based on seeking to maximize signal amplitude or power. However, this does not work for the purpose of isolating a single heart rate source, since regions with multiple sources will tend to generate higher strength signals, and hence will tend to be favored by these known selection algorithms.

The present invention differs in selecting a new depth window based not on signal amplitude, but on the degree of statistical structuredness of the signal (in effect, the degree of statistical non-randomness attributable to the signal, or the strength of statistical patterning identifiable in the signal). Single heart rate sources will lead to more strongly statistically structured signals than mixtures of heart rate signals. Accordingly, the criterion of statistical structure or patterning or non-randomness provides a more effective and reliable criterion for selecting depth windows with isolated heart rate sources, than does signal amplitude or power.

One example in accordance with a first aspect of the invention provides an ultrasound processing unit for use in fetal monitoring for isolating individual heart rate sources within received Doppler ultrasound data. The processing unit is configured to perform in use a number of steps.

Figure 2:
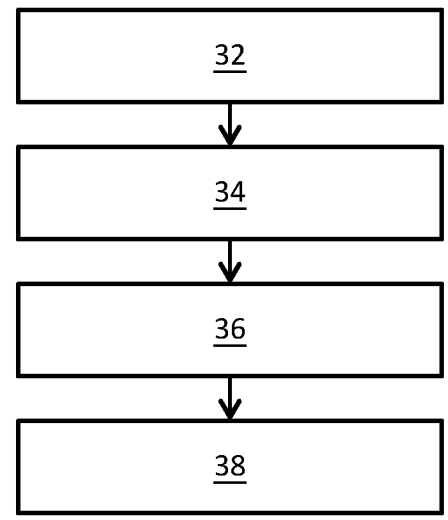
FIG. 2 is a block diagram of steps performed by an example processing unit according to one or more embodiments of the present invention.

FIG. 2 shows in block diagram form the steps performed by the ultrasound processing unit. These will now be outlined in brief, before being explained in more detail.

The ultrasound processing unit is configured to receive 32 input Doppler ultrasound data, corresponding to at least one trial depth region within a uterus region of a subject, having a defined height and depth.

The ultrasound processing unit is further configured to extract 34 an ultrasound signal from the ultrasound data corresponding to the at least one trial depth region, and to determine 36 a defined measure of statistical structure of the signal.

The processing unit is further configured to apply 38 a selection algorithm for determining a depth and height of a new recording region within the subject from which to collect ultrasound signals for measuring a fetal heart rate. The new recording region forms a part of the trail region. The selection algorithm is configured to select a new depth window (being a subpart of the previous window corresponding to the trail region), based on the derived measure of statistical structure for the trial window, and based on seeking a window for which collected ultrasound signals are estimated to have maximized measure of statistical structure.

The selection algorithm may thus perform a maximization procedure to identify height and depth parameters of a new recording depth region (usually being smaller than the trail depth region) which maximizes the measure of statistical structure of signals which will be derived from the window. This is done based on the computed measure of statistical structure for the one or more trial regions.

The method performed by the processing unit is based on deriving at least one pre-defined metric of statistical structure of the one or more trial depth regions. It is also based on then selecting a recording depth region which maximizes this same measure of statistical structure for US signals derived therefrom.

As discussed briefly above, different options exist for the particular measure which is employed. In general, the measure of statistical structure refers to a statistical property or characteristic of the signal. It refers to a statistical structuredness of the signal (a degree of statistical structure). The measure of statistical structure essentially refers to a measure of non-randomness or a degree of statistical patterning of the signal. The terms 'measure of statistical structure' and 'measure of non-randomness' of the signal may be used interchangeably for example.

Statistical measures of signal structure may, by one set of non-limiting examples, be higher-order cumulants such as skewness or kurtosis or combinations thereof, or may be non-polynomial quantities such as negentropy or approximations thereof, or they may be related to the time structure of the signal, such as autocovariance or autocokurtosis. Measures of statistical structure can be used to distinguish unstructured signals (e.g. Gaussian noise or noise without time structure) from less structured signals (e.g. mixtures of pulse rate sources) from, in turn, highly structured signals (single pulse rate sources).

The measure of statistical structure of a given signal may according to one or more further non-limiting examples include: one or more characteristics of a probability density function for the signal; one or more characteristics of a power spectral density function for the signal, and/or a measure of non-stationarity of the variance of the signal.

Certain of these example measures of statistical structure will now be explained in more detail.

Kurtosis is a property derived from the probability density function of the input signal. An estimate of the kurtosis of a signal x with length N can be obtained by calculating $$\text{kurtosis}(x) = \frac{1}{N}\sum_{i=1}^{N}\left(\frac{x_i - m}{\sigma}\right)^4$$

where m is the mean value of x and $\sigma$ is the standard deviation of x. For a signal, x, having Gaussian distribution, this estimate approaches the value 3, while signals with non-Gaussian distribution have values that are larger or smaller than 3.

Subtracting 3 from the estimate and then squaring yields therefore a quantity that is zero for signals with Gaussian distribution, and nonzero for most signals with non-Gaussian distributions. Hence, this quantity may be taken as a measure of statistical structure of the signal: the higher the value, the more deviant is the signal from normal distribution, and hence the more non-random, or statistically structured, is the signal.

The term [kurtosis(x)−3] is sometimes referred to as "excess kurtosis" in literature sources. However, this term may also be referred to simply as "kurtosis" in certain other sources.

This criterion (kurtosis) is related to the probability density function of the signal x.

A further example measure of statistical structure is negentropy. Negentropy is also related to the probability density function of a signal. An estimate of negentropy J of a signal, x, may be obtained by calculating:

$$J(x) = \frac{1}{12}\left(\frac{1}{N}\sum_{i=1}^{N}\left(\frac{x_i-m}{\sigma}\right)^3\right)^2 + \frac{1}{48}\left(\frac{1}{N}\sum_{i=1}^{N}\left(\frac{x_i-m}{\sigma}\right)^4 - 3\right)^2$$

This approximation is given in the book "Independent component analysis" by A. Hyvärinen, J. Karhunen and E. Oja for example.

It is noted that this approximation, as well as the above-outlined estimate of kurtosis may be somewhat sensitive to outliers in the signal due to the use of the third or fourth powers of the signal, x, in the calculation.

In the formula above, optionally the first term may be omitted, as it is zero for any symmetric probability distribution. This leaves a single term based on the squared value of excess kurtosis. This may be considered a simplest estimator of negentropy, and may be employed as a measure of statistical structure in example embodiments.

Negentropy has the property that it is zero for a signal with Gaussian distribution, and greater than zero for any signals with non-Gaussian distributions. Furthermore, its non-zero value increases in direct relation to the degree to which the probability distribution for the signal, x, deviates from Gaussian distribution. Hence, this measure directly quantifies non-Gaussianity. This measure therefore provides a direct measure of statistical structure of a signal.

However, typically, negentropy can only be estimated for signal and often cannot be directly calculated.

It is possible to construct estimators of negentropy that are more robust against outliers. Examples methods for constructing such estimators are given in the book "Independent component analysis" by A. Hyvärinen, J. Karhunen and E. Oja for example.

One simple example estimator for negentropy, J(x), for instance is:

$$J(x) = \frac{24}{16\sqrt{3} - 27}\left(\frac{1}{N}\sum_{i=1}^{N}\left(\exp\left(-\frac{x_i^2}{2}\right) - \sqrt{\frac{1}{2}}\exp\right)\right)^2$$

Estimators of negentropy can be made arbitrarily accurate, but at the cost of increased complexity with increased accuracy. Choosing an estimator for an application is therefore typically a trade-off between the required accuracy and available computing power.

Another example measure of statistical structure of a signal is linear autocovariance.

A simple example measure, which is based on linear autocovariances, is as follows $$C(x) = \frac{1}{N-1}\sum_{i=2}^{N}x_i x_{i-1}$$

This formula may also be found in the book "Independent component analysis" by Oja et al, (see chapter 18 "Methods using time structure").

For this example, the measure C(x) has a value of zero if two adjacent samples of the signal are not correlated, and has a nonzero value if there is some degree of correlation. For comparing two input signal channels, the two signal channel vectors are first normalized by subtracting from each the respective mean and dividing by the respective standard deviation (this eliminates any effect of the power of each channel in the result for C(x)).

For an input signal channel which contains a mixture of source heart rate signals, the absolute value of C(x) will be lower than the highest absolute value of C(x) for an individual heart rate signal source.

In the context of the present invention, the selection algorithm may be configured to search for a recording region within the subject having the highest absolute value of C(x).

It should be noted however that this method may not be fully effective where several heart rate sources are present and have an identical corresponding C(x) (as they cannot be distinguished from each other). However, this situation can be expected to occur only rarely.

A further example measure of statistical structure is non-stationarity of the variance of a signal.

Variance non-stationarity of a signal, x, may be quantified using the fourth-order cumulant (which is one part of the autocokurtosis matrix) as follows:

$$\frac{1}{N-1}\sum_{i=2}^{N}x_i^2 x_{i-1}^2 - \frac{1}{N-1}\left(\sum_{i=2}^{N}x_i^2\right)\left(\sum_{i=2}^{N}x_{i-1}^2\right) - 2\frac{1}{N-1}\left(\sum_{i=2}^{N}x_i x_{i-1}\right)^2$$

The value of this expression is larger for signals, x, that undergo large changes in variance in the interval, N, and smaller where variance is closer to constant.

This expression hence quantifies this nonstationarity of the signal. Usually, mixtures of heart rate signal sources are less nonstationary than separate, individual heart rate sources. Hence variance non-stationarity provides a direct measure of statistical structure of signal. The selection algorithm may in examples search for a recording region within the subject for which acquired signals from the region exhibit the greatest amount of variance nonstationarity.

For comparing different input signal channels, this again requires first normalizing each signal x to zero mean and unit variance over the total range of samples.

Typically, the first term of the formula dominates the two following terms, so it may be possible to omit the two last terms to simplify the calculation.

This formula may also be found in the book "Independent component analysis" by A. Hyvärinen, J. Karhunen and E. Oja, (see chapter 18 "Methods using time structure").

By way of explanation, a stochastic process is said to be stationary if its finite-dimensional distributions are invariant under translations of time. This type of stochastic process can be used to describe a physical system that is in steady state, but still experiences random fluctuations. The concept of stationarity is that as time passes the distribution of the stationary stochastic process remains the same.

The exact calculation of these functions requires an infinite number of signal samples. Therefore, in practice approximations may be used, or quantities may be calculated using the available number of samples that contain some information about the underlying probability distribution.

By way of further non-limiting example, provided by way of illustration, for a signal x that has been pre-processed to have zero-mean (i.e. zero-baseline) and of unity variance (i.e. amplitude of 1, i.e. a normalized signal), examples for statistical measures of structure of a signal include:

$$\text{kurtosis: } kurt(x) = E(x^4) - 3(E(x^2))^2$$

$$\text{Squared kurtosis:}(kurt(x))^2 = [E(x^4) - 3(E(x^2))^2]^2$$

$$\text{Approximation of negentropy: } \frac{1}{12}(E(x^3))^2 + \frac{1}{48}(kurt(x))^2$$

$$\text{Alternative approximation of negentropy: } \left[E\left(\exp\left(-\frac{x^2}{2}\right)\right) - c_1\right]^2$$

Further alternative approximation of negentropy: $[E(\log(\cosh(x))) - c_2]^2$ where E( ) denotes the expectation value operator and $c_1$, $c_2$ denote constants corresponding to the value that the first term would have if x were of Gaussian distribution.

Preferably, the selection algorithm comprises collecting ultrasound signals from a plurality of trial depth regions, and determining at least one measure of statistical structure for each trial region signal.

The selection algorithm in some embodiments may comprise comparing the measures of statistical structure derived for each trial region signal. The measures for the different trial regions may be compared with each other, or they may all be compared to one or more measures derived for one or more reference depth regions.

By comparing the measure(s) of statistical structure of the trial depth window with that/those of the reference depth window, the ultrasound processing unit can determine to what extent the height and depth parameters of the trial region should be adjusted in order to maximize the statistical structure for signals in the recording window.

Where multiple depth regions are trialed and their signal structure measures compared with one another, this provides a spectrum of different statistical structure values and the corresponding depth parameters which yielded them. This allows a relationship between the measure of statistical structure and each of the height and depth parameters to be derived. From this relationship, it is possible to derive, e.g. extrapolate, or interpolate, a set of parameters which are likely to yield ultrasound signals with maximal signal structure.

Alternatively, the selection algorithm may comprise an iterative process, wherein ultrasound signals are collected one at a time from successive trial depth regions. For each new trial depth region, a measure of statistical structure is derived for the ultrasound signal. This may then be compared with the measure of statistical structure for signals of one or more previously trialed depth regions, and based on the result, the algorithm determines whether, and in what way, the height and depth parameters should be adjusted for the next trial region in order to increase the measure of statistical structure of signals derived therefrom.

The selection algorithm may for each new trial region, based on the comparison with the one or more previous regions, determine whether the current region has maximized measure of statistical structure. This may for instance be based on plotting or otherwise computing an ongoing change in the statistical structure measure as a function of incrementing trial region index. When it is detected that the statistical structure measure has reached a turning point, e.g. the second derivative of said computed function is zero or approximately zero, the selection algorithm may simply use the height and depth parameters of the current trial depth region for the new recording region.

Alternatively, the selection algorithm may detect for each new trial region whether the measure of statistical structure for the region is within some threshold proximity to that for the previous trial region, in which case the height and depth parameters for the new region are selected for the final recording depth region.

Embodiments of the present invention involve controlling a depth region within the subject from which ultrasound signals are extracted. The general procedure for performing this will now be briefly outlined.

Doppler ultrasound data is obtained using an ultrasound transducer unit. This may be controlled by the ultrasound processing unit, or may be performed separately. In preferred examples, the ultrasound processing unit of the invention is operatively coupleable in use with an ultrasound processing unit, and is adapted to control the transducer unit to acquire ultrasound data. The processing unit is preferably operable to adjust acquisition or other acoustic settings of the ultrasound transducer unit for thereby adjusting a depth region from which ultrasound signals are acquired.

The transducer unit may comprise a plurality of ultrasound transducers or a single transducer. The received ultrasound data is typically representative of a plurality of different depths within the targeted body. From this data, there may be extracted one or more signal channels corresponding to signals for one or more specific depths in the scanned body.

In more detail, in operation, ultrasound pulses may transmitted by an ultrasound receive/transmit unit into the body being probed, i.e. the uterus region of the subject. The pulses are transmitted at a defined frequency over a defined transmit window, or recurrent set of transmit windows. The receive/transmit unit comprises one or more ultrasound transducers for generating and sensing ultrasound signals. It is a form of ultrasound transducer unit, but without comprising signal processing components (which are comprised externally to the unit in this example).

Reflected ultrasound signals are then received back at the ultrasound receive-transmit unit. Reflections will be received at the receive-transmit unit at different time points depending upon the depth from which the signal is reflected. As the propagation speed of ultrasound in tissue is known (approximately 1000 meters/second), the time delay between transmission and reception may be mapped to the distance the ultrasound pulse has travelled. This distance is then proportional to the depth.

In some examples, signals are transmitted in a single direction, and ultrasound signals received and gated corresponding to different depths within a resulting single cylindrical beam field.

In further examples, the ultrasound transducer unit may comprise an array of individual ultrasound transmitters, and wherein a control means is configured to apply beamforming using the array, to control a directionality of a generated ultrasound beam.

In either case, the resulting ultrasound data may be amplified by an amplifier, and then split into a plurality of signal channels, corresponding to different depth regions within the subject. Alternatively, if only a single depth region is sought, the channel corresponding to said single depth region may be extracted from the set of channels.

Signals corresponding to different depths may be separated for example by gating the incoming signal over different temporal receive windows, each gated signal then providing a different input signal channel corresponding to a different depth.

In some examples, the duration of, and timing between, transit pulses and receive windows can be adjusted so that receive signals from specific desired depths can be obtained, these then being gated over the appropriate time windows to provide different depth signals on each depth channel.

Optionally, the gating pulses for the channels may be produced by digital logic (e.g. a microcontroller, FPGA or similar) included the receive-transmit (or ultrasound transducer) unit. The gated signal may subsequently be sampled with an analog-to-digital converter. A relatively low sampling rate may be used (for example several hundred to several thousand Hz).

The skilled person in this field will be aware of numerous approaches to gating signals to extract channels corresponding to different depths within the probed body.

The one or more gated depth signals each provide a respective input signal channel (or 'depth channel').

Pre-processing steps are applied to each of the one or more depth signal channels. These may be applied after separating the different input signal channels or before.

In particular, a demodulation and signal integration may be applied to the input signals of each input signal channel. Demodulation generates a signal with a frequency equal to the Doppler (frequency) shift of the measured Doppler signal, compared to the original transmitted signal.

Bandpass filtering may be applied to each depth signal channel. The filtering is configured to select the frequency component of the incoming signal within the frequency range expected for the fetal heartbeat measurement. This ensures only the relevant frequency component of the data is retained, reducing overall noise.

An envelope demodulator may additionally be applied in some examples (not shown). This extracts for each depth signal channel an envelope signal corresponding to the change in signal strength (e.g. intensity or variance), as a function of time, for the selected (filtered) frequency range.

In certain examples, the demodulation function might be incorporated into a digital microprocessor comprised by the ultrasound transducer unit. In this case, the reflection of the transmitted pulse may be sampled with an analog-to-digital converter at a high sampling rate (several times the frequency of transmitted ultrasound pulse, e.g. several MHz), and digital logic or software in the transducer unit may demodulate the received signal and calculate a signal value for each depth channel. This may remove the need for gating pulses and analog demodulation circuitry.

Providing a digital microprocessor capable of analogue to digital conversion at the required resolution and speed to provide processing synchronously with signal acquisition may be challenging with current microprocessor technology. In alternative examples, splitting of the depth channels may be performed instead using a dedicated analogue to digital (A/D) converter included in the ultrasound transducer unit. The A/D converter should in this case operate synchronously, meaning the ultrasound frequency matches (is preferably identical to) the A/D conversion frequency.

One example embodiment of the ultrasound processing unit will now be briefly outlined.

An ultrasound processing unit is provided as described above, and is operatively coupleable in use with an ultrasound transducer unit. The ultrasound processing unit, in combination with the transducer unit is operable to record Doppler ultrasound signals from at least two depth regions within a given subject. The depth regions may have adjustable height and depth parameters, or may have fixed height and depth parameters.

The ultrasound processing unit records Doppler ultrasound signals from each depth region and calculates measures of statistical structure for each. Based on a comparison of the value(s) of each signal, the processing unit either adjusts the size and depth parameters (or, correspondingly, the starting depth and end depth) of the recorded depth region in order to increase the degree of structure for the final recording window for which fetal heart rate (FHR) signals will be acquired. Alternatively the unit may simply select the one of the available depth window channels with the greatest measure of statistical structure for use as the new recording window for collecting signals for FHR calculations The ultrasound processor may compare the different depth signal channels using a signal structure criterion such as normalized kurtosis or negentropy (or any of the other examples criteria outlined above). These measures are not influenced by the (average) amplitude of the signal, and for this reason can be used to distinguish a channel that contains only or mostly one independent pulse rate signal from a channel that contains a mixture of pulse rate signals or no pulse rate signals at all.

By way of one example, by seeking to maximize for an approximation negentropy of the depth channel signal, the selection algorithm will have the effect of adjusting the window size and depth position until only one independent pulse rate signal is being recorded.

Examples in accordance with a further aspect of the invention provide an ultrasound apparatus comprising: an ultrasound processing unit in accordance with any example or embodiment outlined above or described below, or in accordance with any claim of this application and one or more ultrasound transducers 76, operatively coupled to the ultrasound processing unit, for providing the Doppler ultrasound data to the ultrasound processing unit, and optionally having adjustable acquisition settings for fixing a depth window of the acquired ultrasound data.

The apparatus may for example comprise an ultrasound probe unit, the probe unit incorporating the ultrasound processing unit and the one or more ultrasound transducers. For instance, the probe may comprise a housing incorporating the one or more ultrasound transducers and the ultrasound processing unit.

Figure 3:
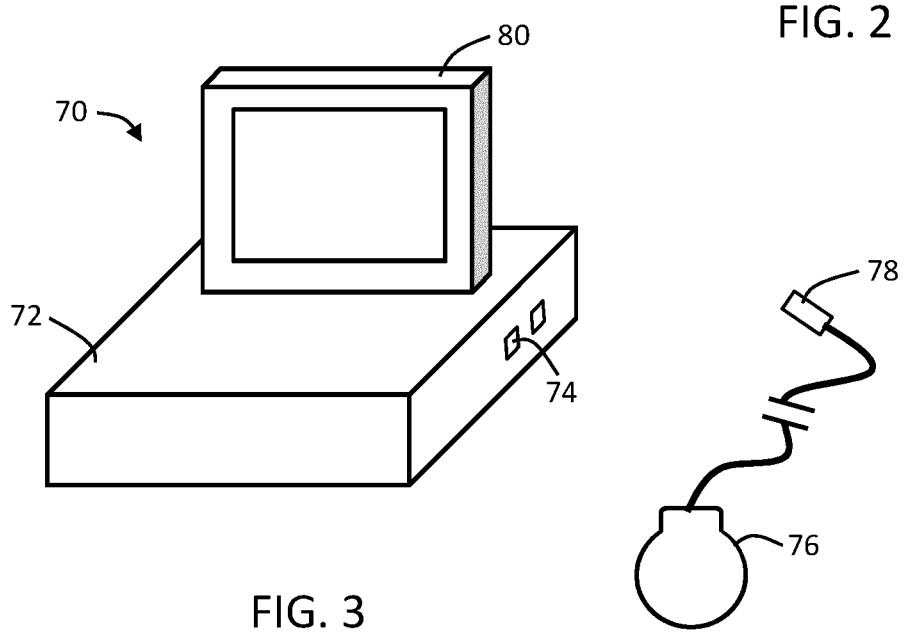
FIG. 3 shows an example ultrasound system according to one or more embodiments.

Examples in accordance with a further aspect of the invention provide a patient monitoring system. An example patient monitoring system 70 in accordance with one or more embodiments is shown in FIG. 3.

The patient monitoring system 70 comprises an ultrasound processing unit in accordance with any example or embodiment outlined above or described below, or in accordance with any claim of this application. In the example shown the ultrasound processing unit is incorporated internally within a base station unit 72. In other examples however, the ultrasound processing unit may be incorporated locally within an ultrasound transducer unit 76 with which the base station unit is connected or connectable.

The patient monitoring system 70 further comprises a connection interface in the form of an input connector port 74 for connecting in use to an ultrasound transducer unit 76 for receiving the input Doppler ultrasound data, or data derived therefrom. An example ultrasound transducer unit 76 for connecting in use to the base station is shown in FIG. 3. The transducer unit comprises an output connector 78 shaped to engage with the input connector 74 of the base station.

Where the ultrasound processing unit is included in the base station 72, the input connector 74 may be coupled to the ultrasound processing unit to transfer the received ultrasound data.

The connector 74 is shown as a wired connector port in FIG. 3. In other examples, the connector may comprise a wireless connection interface for connecting to a wireless ultrasound probe.

The patient monitoring system 70 may further comprise an ultrasound transducer unit 76 coupled to said input connector. The transducer unit may be an ultrasound probe for example.

The patient monitoring system in the present example further includes a display 80 operably coupled to the ultrasound processing unit of the base station 72 for displaying results of the analysis procedure performed, e.g. displaying a visual representation of the one or more second output signals.

The patient monitoring system 70 may further include a controller adapted to control acquisition of ultrasound data by a connected transducer unit in use.

The controller may control transmit and receive circuits of the ultrasound transducer unit to acquire the ultrasound signals representative of different depths. The controller may control durations of, and timings between, transmit pulses and receive windows. The controller may control gating of the input Doppler signal data over defined time windows to thereby separate or extract different input signal channels corresponding to one or more specific depths within the subject's tissue.

In some examples said controller may be comprised locally within the ultrasound transducer unit, or the control steps performed by it may be performed locally at the ultrasound transducer unit.

As mentioned above, the ultrasound transducer unit may comprise the ultrasound processing unit. It may be an ultrasound probe unit for instance incorporating one or more ultrasound transducers and an ultrasound processing unit operatively coupled with the processing unit. The ultrasound transducer unit may locally perform at least a subset of the ultrasound data pre-processing steps and/or control steps described above.

The patient monitoring system may take different forms to that described above. For example the patient monitoring system may comprise a monitoring station (e.g. a trolley-type monitoring station), comprising a display, and being connectable with an ultrasound transducer unit.

In any example, the patient monitoring system may be connectable with any number of further sensors or data sources for monitoring the same patient or different patients.

Examples in accordance with a further aspect of the invention provide An ultrasound processing method for use in fetal monitoring for isolating an individual heart rate source within received Doppler ultrasound data, the method comprising:

receiving 32 input Doppler ultrasound data, corresponding to at least one trial depth region within a uterus region of a subject, having a defined height and depth;

extracting 34 an ultrasound signal from the ultrasound data corresponding to the at least one trial depth region, and determining 36 a defined measure of statistical structure of the signal;

applying 38 a selection algorithm for determining a depth and height of a new recording region within the subject from which to collect ultrasound signals for measuring a fetal heart rate, the selection algorithm configured to select the window based on the determined measure of statistical structure for the trial region, and based on maximizing the measure of statistical structure of signals acquired from the new recording region.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. An ultrasound processor for use in fetal monitoring for isolating individual heart rate sources within received Doppler ultrasound data, the ultrasound processor configured to:
receive input Doppler ultrasound data, corresponding to at least one trial depth region within a uterus region of a subject, said region having a defined height and depth;
extract an ultrasound signal from the ultrasound data corresponding to the at least one trial depth region, and determine a defined measure of statistical structure of the ultrasound signal, the measure of statistical structure corresponding to an intrinsic statistical property or characteristic of the ultrasound signal; and
apply a selection algorithm for determining a depth and height of a new recording region within the subject from which to collect ultrasound signals for measuring a fetal heart rate, the selection algorithm configured to select the recording region based on the determined measure of statistical structure for the trial region, and based on maximizing the measure of statistical structure of ultrasound signals acquired from the new recording region.

2. The ultrasound processor as claimed in claim 1, wherein the selection algorithm comprises collecting ultrasound signals from a plurality of trial depth regions, and determining the defined measure of statistical structure for each trial region ultrasound signal.

3. The ultrasound processor as claimed in claim 2, wherein the selection algorithm comprises a comparison of the measures of statistical structure derived for each trial region ultrasound signal.

4. The ultrasound processor as claimed in claim 3, wherein said comparison comprises comparing the measures of statistical structure for the different ultrasound signals with each other, and/or comprises comparing the measure of statistical structure for each trial region with a further measure derived for a reference depth region ultrasound signal.

5. The ultrasound processor as claimed in claim 2, wherein the selection algorithm comprises an iterative process, comprising iteratively collecting ultrasound signals from successive trial depth regions, deriving a measure of statistical structure for each, and comparing the derived measure with that derived for one or more previously trialed windows.

6. The ultrasound processor as claimed in claim 1, wherein the measure of statistical structure of a given ultrasound signal includes: one or more characteristics of a probability density function for the ultrasound signal; one or more characteristics of a power spectral density function for the ultrasound signal, and/or a measure of non-stationarity of the variance of the ultrasound signal.

7. The ultrasound processor as claimed in claim 1, wherein the measure of statistical structure includes an approximation of one or more of: kurtosis or a derivative thereof, negentropy, autocovariance, or autocokurtosis.

8. The ultrasound processor as claimed in claim 1, wherein the ultrasound processor is operatively coupleable in use with an ultrasound transducer unit, for acquiring the Doppler ultrasound data, and for adjusting acquisition settings of the transducer unit for thereby adjusting a depth region from which ultrasound signals are acquired.

9. An ultrasound apparatus comprising:
an ultrasound processor as claimed in claim 1; and
one or more ultrasound transducers, operatively coupled to the ultrasound processing unit, for providing the Doppler ultrasound data to the ultrasound processing unit.

10. The ultrasound apparatus as claimed in claim 9, wherein the apparatus comprises an ultrasound probe unit, the probe unit incorporating the ultrasound processing unit and the one or more ultrasound transducers.

11. A patient monitoring system comprising:
an ultrasound processing unit as claimed in claim 1; and
a connection interface for connecting in use to an ultrasound transducer unit.

12. The patient monitoring system as claimed in claim 11, further comprising an ultrasound transducer unit coupled to said connection interface.

13. The patient monitoring system as claimed in claim 11, further including a controller adapted to control acquisition of ultrasound data by a connected transducer unit in use.

14. An ultrasound processing method for use in fetal monitoring for isolating an individual heart rate source within received Doppler ultrasound data, the method comprising:
- receiving input Doppler ultrasound data, corresponding to at least one trial depth region within a uterus region of a subject, having a defined height and depth;
- extracting an ultrasound signal from the ultrasound data corresponding to the at least one trial depth region, and determining a defined measure of statistical structure of the ultrasound signal, the measure of statistical structure corresponding to an intrinsic statistical property or characteristic of the ultrasound signal;
- applying a selection algorithm for determining a depth and height of a new recording region within the subject from which to collect ultrasound signals for measuring a fetal heart rate, the selection algorithm configured to select the new recording region based on the determined measure of statistical structure for the trial region, and based on maximizing the measure of statistical structure of ultrasound signals acquired from the new recording region.

15. The apparatus of claim 9, wherein the one or more ultrasound transducers have adjustable acquisition settings for fixing a depth window of the acquired ultrasound data.

* * * * *